US012697199B2

(12) United States Patent
Felix et al.

(10) Patent No.: US 12,697,199 B2
(45) Date of Patent: Aug. 4, 2026

(54) PROSTHETIC REPAIR FABRIC

(71) Applicant: Davol Inc., Warwick, RI (US)

(72) Inventors: Augustus Felix, Cranston, RI (US);
Michael Ligeikis, Marlton, NJ (US)

(73) Assignee: Davol Inc., Warwick, RI (US)

( * ) Notice: Subject to any disclaimer, the term of this patent is extended or adjusted under 35 U.S.C. 154(b) by 1127 days.

(21) Appl. No.: 16/907,104

(22) Filed: Jun. 19, 2020

(65) Prior Publication Data

US 2021/0393390 A1 Dec. 23, 2021

(51) Int. Cl.
*A61F 2/00* (2006.01)

(52) U.S. Cl.
CPC .... *A61F 2/0063* (2013.01); *A61F 2002/0068* (2013.01)

(58) Field of Classification Search
CPC ...................... A61F 2/0063; A61F 2002/0068
See application file for complete search history.

(56) References Cited

U.S. PATENT DOCUMENTS

| | | | |
|---|---|---|---|
| 2,671,444 A | 3/1954 | Pease | |
| 3,054,406 A | 9/1962 | Usher | |
| 3,108,357 A | 10/1963 | Liebig | |
| 3,124,136 A | 3/1964 | Usher | |
| 3,272,204 A | 9/1966 | Artandi et al. | |
| 3,276,448 A | 10/1966 | Kronenthat | |
| 3,448,595 A | 6/1969 | Baltzer et al. | |
| 3,463,158 A | 8/1969 | Schmitt et al. | |

| | | | |
|---|---|---|---|
| 3,559,214 A | 2/1971 | Pangman | |
| 3,805,301 A | 4/1974 | Liebig | |
| 3,853,462 A | 12/1974 | Smith | |
| 3,875,928 A | 4/1975 | Angelchik | |
| 3,878,565 A | 4/1975 | Sauvage | |
| 3,945,052 A | 3/1976 | Liebig | |
| 3,986,828 A | 10/1976 | Hoffmann et al. | |
| 3,988,411 A | 10/1976 | Capozza | |
| 4,015,451 A | 4/1977 | Gajjar | |
| 4,032,993 A | 7/1977 | Coquard et al. | |
| 4,064,712 A | 12/1977 | Sayre et al. | |
| 4,141,087 A | 2/1979 | Shalaby et al. | |

(Continued)

FOREIGN PATENT DOCUMENTS

| | | |
|---|---|---|
| AU | 593 267 B2 | 2/1990 |
| CA | 2 900 682 A1 | 9/2014 |

(Continued)

OTHER PUBLICATIONS

Sanbhal et al. "Physical structure and mechanical properties of knitted hernia mesh materials: A review" Journal of Industrial Textiles. 2018; 48(1):333-360. doi:10.1177/1528083717690613.*

(Continued)

*Primary Examiner* — Jing Rui Ou
(74) *Attorney, Agent, or Firm* — Wolf, Greenfield & Sacks, P.C.

(57) ABSTRACT

The repair fabric includes a dual bar warp knit mesh for use in repairing soft tissue and muscle wall defects, including hernia repair and chest wall reconstruction. The repair fabric may be produced according to a first bar pattern chain of 4/2 4/6 4/2 6/8 6/4 6/8 of first filaments and a second bar pattern chain of 6/8 2/0 6/8 4/2 8/10 4/2 of second filaments. The diameter of the first filaments being different from the diameter of the second filaments.

38 Claims, 3 Drawing Sheets

(56) References Cited

U.S. PATENT DOCUMENTS

| | | | |
|---|---|---|---|
| 4,193,137 A | 3/1980 | Heck |
| 4,345,414 A | 8/1982 | Bornat et al. |
| 4,347,847 A | 9/1982 | Usher |
| 4,385,093 A | 5/1983 | Hubis |
| 4,391,106 A | 7/1983 | Schafer et al. |
| 4,403,604 A | 9/1983 | Wilkinson |
| 4,441,215 A | 4/1984 | Kaster |
| 4,452,245 A | 6/1984 | Usher |
| 4,476,697 A | 10/1984 | Schafer et al. |
| 4,478,665 A | 10/1984 | Hubis |
| 4,499,139 A | 2/1985 | Schortman |
| 4,545,082 A | 10/1985 | Hood |
| 4,555,378 A | 11/1985 | Martin et al. |
| 4,573,999 A | 3/1986 | Netto |
| 4,576,608 A | 3/1986 | Homsy |
| 4,596,728 A | 6/1986 | Yang et al. |
| 4,633,873 A | 1/1987 | Dumican et al. |
| 4,652,264 A | 3/1987 | Dumican |
| 4,655,221 A | 4/1987 | Devereux |
| 4,693,720 A | 9/1987 | Scharnberg |
| 4,695,500 A | 9/1987 | Dyer et al. |
| 4,728,328 A | 3/1988 | Hughes |
| 4,769,038 A | 9/1988 | Bendavid et al. |
| 4,838,884 A | 6/1989 | Dumican et al. |
| 4,841,948 A | 6/1989 | Bauer |
| 4,883,486 A | 11/1989 | Kapadia et al. |
| 4,902,508 A | 2/1990 | Badylak et al. |
| 4,923,470 A | 5/1990 | Dumican |
| 4,955,907 A | 9/1990 | Ledergerber |
| 4,997,440 A | 3/1991 | Dumican |
| 5,002,551 A | 3/1991 | Linksy et al. |
| 5,007,916 A | 4/1991 | Linsky et al. |
| 5,061,277 A | 10/1991 | Carpentier et al. |
| 5,092,884 A | 3/1992 | Devereux et al. |
| 5,112,352 A | 5/1992 | Novack |
| 5,116,360 A | 5/1992 | Pinchuk et al. |
| 5,116,370 A | 5/1992 | Foglietti |
| 5,146,933 A | 9/1992 | Boyd |
| 5,147,398 A | 9/1992 | Lynn et al. |
| 5,178,630 A | 1/1993 | Schmitt |
| 5,222,987 A | 6/1993 | Jones |
| 5,236,454 A | 8/1993 | Miller |
| 5,258,000 A | 11/1993 | Gianturco |
| 5,282,856 A | 2/1994 | Ledergerber |
| 5,292,328 A | 3/1994 | Hain et al. |
| 5,304,187 A | 4/1994 | Smith |
| 5,306,296 A | 4/1994 | Wright et al. |
| 5,316,147 A | 5/1994 | Weber-Unger |
| 5,326,355 A | 7/1994 | Landi |
| 5,356,429 A | 10/1994 | Seare |
| 5,356,432 A | 10/1994 | Rutkow et al. |
| 5,366,460 A | 11/1994 | Eberbach |
| 5,366,504 A | 11/1994 | Andersen et al. |
| 5,368,602 A | 11/1994 | de la Torre |
| 5,383,477 A | 1/1995 | DeMatteis |
| 5,383,925 A | 1/1995 | Schmitt |
| 5,424,117 A | 6/1995 | Heiman et al. |
| 5,433,996 A | 7/1995 | Kranzler et al. |
| 5,443,508 A | 8/1995 | Giampapa |
| 5,456,711 A | 10/1995 | Hudson |
| 5,456,720 A | 10/1995 | Schultz et al. |
| 5,458,636 A | 10/1995 | Brancato |
| 5,461,885 A | 10/1995 | Yokoyama et al. |
| 5,462,781 A | 10/1995 | Zukowski |
| 5,466,258 A | 11/1995 | Rubin |
| 5,468,242 A | 11/1995 | Reisberg |
| 5,480,423 A | 1/1996 | Ravenscroft et al. |
| 5,554,437 A | 9/1996 | Gupta et al. |
| 5,569,273 A | 10/1996 | Titone et al. |
| 5,584,884 A | 12/1996 | Pignataro |
| 5,593,441 A | 1/1997 | Lichtenstein et al. |
| 5,611,127 A | 3/1997 | Ceriani et al. |
| 5,674,279 A | 10/1997 | Wright et al. |
| 5,676,146 A | 10/1997 | Scarborough |
| 5,683,809 A | 11/1997 | Freeman et al. |
| 5,695,525 A | 12/1997 | Mulhauser et al. |
| 5,702,459 A | 12/1997 | Hummer et al. |
| 5,716,404 A | 2/1998 | Vacanti et al. |
| 5,716,408 A | 2/1998 | Eldridge et al. |
| 5,716,409 A | 2/1998 | Debbas |
| 5,725,577 A | 3/1998 | Saxon |
| 5,732,572 A | 3/1998 | Litton |
| 5,743,917 A | 4/1998 | Saxon |
| 5,766,246 A | 6/1998 | Mulhauser et al. |
| 5,769,864 A | 6/1998 | Kugel |
| 5,796,462 A | 8/1998 | Roffman et al. |
| 5,865,728 A | 2/1999 | Moll et al. |
| 5,895,424 A | 4/1999 | Steele, Sr. et al. |
| 5,916,225 A | 6/1999 | Kugel |
| 5,948,020 A | 9/1999 | Yoon et al. |
| 5,954,767 A | 9/1999 | Pajotin et al. |
| 5,972,007 A | 10/1999 | Sheffield et al. |
| 5,990,378 A | 11/1999 | Ellis |
| 6,004,333 A | 12/1999 | Sheffield et al. |
| 6,024,763 A | 2/2000 | Lenker et al. |
| 6,042,592 A | 3/2000 | Schmitt |
| 6,066,776 A | 5/2000 | Goodwin et al. |
| 6,066,777 A | 5/2000 | Benchetrit |
| 6,074,419 A | 6/2000 | Healy et al. |
| 6,090,116 A | 7/2000 | D'Aversa et al. |
| 6,096,044 A | 8/2000 | Boyd et al. |
| 6,113,623 A | 9/2000 | Sgro |
| 6,113,641 A | 9/2000 | Leroy et al. |
| 6,120,434 A | 9/2000 | Kimura et al. |
| 6,120,539 A | 9/2000 | Eldridge et al. |
| 6,136,024 A | 10/2000 | Shimizu |
| 6,143,025 A | 11/2000 | Stobic et al. |
| 6,162,537 A | 12/2000 | Martin et al. |
| 6,162,962 A | 12/2000 | Hinsch et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,176,875 B1 | 1/2001 | Lenker et al. |
| 6,179,872 B1 | 1/2001 | Bell et al. |
| 6,192,944 B1 | 2/2001 | Grennhalgh |
| 6,214,020 B1 | 4/2001 | Mulhauser et al. |
| 6,221,102 B1 | 4/2001 | Baker et al. |
| 6,224,616 B1 | 5/2001 | Kugel |
| 6,241,768 B1 | 6/2001 | Agarwal et al. |
| 6,251,132 B1 | 6/2001 | Ravenscroft et al. |
| 6,253,581 B1 | 7/2001 | Rhode et al. |
| 6,258,124 B1 | 7/2001 | Darois et al. |
| 6,264,702 B1 | 7/2001 | Ory et al. |
| 6,268,544 B1 | 7/2001 | Court et al. |
| 6,270,530 B1 | 8/2001 | Eldridge et al. |
| 6,280,453 B1 | 8/2001 | Kugel et al. |
| 6,287,293 B1 | 9/2001 | Jones et al. |
| 6,287,316 B1 | 9/2001 | Agarwal et al. |
| 6,290,708 B1 | 9/2001 | Kugel et al. |
| 6,306,154 B1 | 10/2001 | Hudson et al. |
| 6,312,442 B1 | 11/2001 | Kieturakis et al. |
| 6,312,456 B1 | 11/2001 | Kranz et al. |
| 6,315,791 B1 | 11/2001 | Gingras et al. |
| 6,319,264 B1 | 11/2001 | Tormala et al. |
| 6,368,541 B1 | 4/2002 | Pajotin et al. |
| 6,375,662 B1 | 4/2002 | Schmitt |
| 6,383,201 B1 | 5/2002 | Dong |
| 6,391,060 B1 | 5/2002 | Ory et al. |
| 6,408,656 B1 | 6/2002 | Ory et al. |
| 6,443,964 B1 | 9/2002 | Ory et al. |
| 6,447,551 B1 | 9/2002 | Goldmann |
| 6,451,139 B1 | 9/2002 | Weber-Unger et al. |
| 6,488,801 B1 | 12/2002 | Bodaghi et al. |
| 6,521,555 B1 | 2/2003 | Bodaghi et al. |
| 6,537,313 B2 | 3/2003 | Ketharanathan |
| 6,540,773 B2 | 4/2003 | Dong |
| 6,547,820 B1 | 4/2003 | Staudenmeier |
| 6,554,855 B1 | 4/2003 | Dong |
| 6,596,002 B2 | 7/2003 | Therin et al. |
| 6,610,006 B1 | 8/2003 | Amid et al. |
| 6,630,414 B1 | 10/2003 | Matsumoto |
| 6,638,284 B1 | 10/2003 | Rousseau et al. |
| 6,652,574 B1 | 11/2003 | Jayaraman |
| 6,652,595 B1 | 11/2003 | Nicolo |

(56) References Cited

U.S. PATENT DOCUMENTS

| | | | |
|---|---|---|---|
| 6,668,598 B2 | 12/2003 | Miyake et al. |
| 6,669,706 B2 | 12/2003 | Schmitt et al. |
| 6,673,102 B1 | 1/2004 | Vonesh et al. |
| 6,679,913 B2 | 1/2004 | Homsy |
| 6,706,376 B1 | 3/2004 | von Fransecky |
| 6,711,919 B1 | 3/2004 | Arnold et al. |
| 6,723,133 B1 | 4/2004 | Pajotin |
| 6,726,696 B1 | 4/2004 | Houser et al. |
| 6,736,823 B2 | 5/2004 | Darois et al. |
| 6,737,371 B1 | 5/2004 | Planck et al. |
| 6,740,122 B1 | 5/2004 | Pajotin |
| 6,755,867 B2 | 6/2004 | Rousseau |
| 6,755,868 B2 | 6/2004 | Rousseau |
| 6,783,554 B2 | 8/2004 | Amara et al. |
| 6,790,213 B2 | 9/2004 | Cherok et al. |
| 6,800,082 B2 | 10/2004 | Rousseau |
| 6,840,067 B2 | 1/2005 | Mass et al. |
| 6,841,492 B2 | 1/2005 | Bhatnagar et al. |
| 6,848,281 B2 | 2/2005 | Ishihara et al. |
| 6,946,003 B1 | 9/2005 | Wolowacz et al. |
| 6,971,252 B2 | 12/2005 | Therin et al. |
| 7,198,638 B2 | 4/2007 | Dong |
| 7,364,587 B2 | 4/2008 | Dong et al. |
| 7,402,174 B2 | 7/2008 | Dong |
| 7,614,258 B2 | 11/2009 | Cherok et al. |
| 7,900,484 B2 | 3/2011 | Cherok et al. |
| 8,956,394 B1 * | 2/2015 | McDonnell ............. D04C 1/06 |
| | | | 606/86 R |
| 9,416,471 B2 | 8/2016 | Trabucco et al. |
| 9,603,698 B2 | 3/2017 | Kerr et al. |
| 10,335,257 B2 | 7/2019 | Rizk et al. |
| 11,413,129 B2 | 8/2022 | Felix et al. |
| 2001/0027347 A1 | 10/2001 | Rousseau |
| 2001/0034528 A1 | 10/2001 | Foerster et al. |
| 2001/0049538 A1 | 12/2001 | Trabucco |
| 2001/0053919 A1 | 12/2001 | Kieturakis et al. |
| 2001/0056303 A1 | 12/2001 | Caneiro et al. |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0052654 A1 | 5/2002 | Darois et al. |
| 2002/0082707 A1 | 6/2002 | Homsy |
| 2002/0095218 A1 | 7/2002 | Carr et al. |
| 2002/0103542 A1 | 8/2002 | Bilbo |
| 2002/0115369 A1 | 8/2002 | Yokoyama |
| 2002/0116070 A1 | 8/2002 | Amara et al. |
| 2002/0119177 A1 | 8/2002 | Bowman et al. |
| 2002/0120348 A1 | 8/2002 | Melican et al. |
| 2002/0147457 A1 | 10/2002 | Rousseau |
| 2002/0160679 A1 | 10/2002 | Yoon |
| 2002/0187694 A1 | 12/2002 | Brighton et al. |
| 2002/0193885 A1 | 12/2002 | Legeay et al. |
| 2002/0198588 A1 | 12/2002 | Armstrong et al. |
| 2003/0004581 A1 | 1/2003 | Rousseau |
| 2003/0028239 A1 | 2/2003 | Dong |
| 2003/0040809 A1 | 2/2003 | Goldmann et al. |
| 2003/0065248 A1 | 4/2003 | Lau et al. |
| 2003/0078602 A1 | 4/2003 | Rousseau |
| 2003/0100954 A1 | 5/2003 | Schuldt-Hempe et al. |
| 2003/0100955 A1 | 5/2003 | Greenawalt et al. |
| 2003/0114866 A1 | 6/2003 | Ulmsten et al. |
| 2003/0125796 A1 | 7/2003 | Dong |
| 2003/0130745 A1 | 7/2003 | Cherok et al. |
| 2003/0130747 A1 | 7/2003 | Abraham et al. |
| 2003/0134100 A1 | 7/2003 | Mao et al. |
| 2003/0149464 A1 | 8/2003 | Dong |
| 2003/0149490 A1 | 8/2003 | Ashman |
| 2003/0158607 A1 | 8/2003 | Carr et al. |
| 2003/0176912 A1 | 9/2003 | Chuter et al. |
| 2003/0181988 A1 | 9/2003 | Rousseau |
| 2003/0187516 A1 | 10/2003 | Amid et al. |
| 2003/0204235 A1 | 10/2003 | Edens et al. |
| 2003/0204241 A1 | 10/2003 | Dong |
| 2004/0029478 A1 | 2/2004 | Planck et al. |
| 2004/0034373 A1 | 2/2004 | Schuldt-Hempe et al. |

| | | | |
|---|---|---|---|
| 2004/0049260 A1 | 3/2004 | Dong |
| 2004/0054376 A1 | 3/2004 | Ory et al. |
| 2004/0059356 A1 | 3/2004 | Gingras |
| 2004/0138762 A1 | 7/2004 | Therin et al. |
| 2004/0172048 A1 | 9/2004 | Browning |
| 2004/0176658 A1 | 9/2004 | McMurray |
| 2004/0181288 A1 | 9/2004 | Darois et al. |
| 2004/0185734 A1 | 9/2004 | Gray et al. |
| 2004/0209538 A1 | 10/2004 | Klinge et al. |
| 2004/0211225 A1 | 10/2004 | Dickerson |
| 2004/0215219 A1 | 10/2004 | Eldridge et al. |
| 2004/0220610 A1 | 11/2004 | Kreidler et al. |
| 2004/0260315 A1 | 12/2004 | Dell et al. |
| 2005/0010239 A1 | 1/2005 | Chefitz |
| 2005/0021058 A1 | 1/2005 | Negro |
| 2005/0043818 A1 | 2/2005 | Bellon Caneiro et al. |
| 2005/0070829 A1 | 3/2005 | Therin et al. |
| 2005/0070930 A1 | 3/2005 | Kammerer |
| 2005/0222591 A1 | 10/2005 | Gingras et al. |
| 2005/0228408 A1 | 10/2005 | Fricke et al. |
| 2008/0147198 A1 | 6/2008 | Cherok et al. |
| 2009/0275974 A1 * | 11/2009 | Marchand ........ A61B 17/12118 |
| | | | 87/8 |
| 2010/0049222 A1 | 2/2010 | Cherok et al. |
| 2011/0288568 A1 * | 11/2011 | Capuzziello .......... A61F 2/0063 |
| | | | 606/151 |
| 2011/0307077 A1 | 12/2011 | Pfeiffer et al. |
| 2013/0178875 A1 | 7/2013 | Horton et al. |
| 2013/0317623 A1 * | 11/2013 | Trabucco ............... D04B 21/12 |
| | | | 623/23.72 |
| 2016/0058533 A1 | 3/2016 | Schuldt-Hempe et al. |
| 2017/0216018 A1 | 8/2017 | Limem et al. |
| 2019/0247180 A1 | 8/2019 | Limem et al. |
| 2021/0393389 A1 | 12/2021 | Felix et al. |

FOREIGN PATENT DOCUMENTS

| | | | |
|---|---|---|---|
| DE | 892 663 C | 10/1953 |
| DE | 40 13 447 C1 | 2/1992 |
| DE | 92 12 261 U1 | 12/1992 |
| DE | 10 2014 012 717 A1 | 3/2016 |
| EP | 0 194 192 A1 | 9/1986 |
| EP | 0 212 604 A2 | 3/1987 |
| EP | 0 303 496 A1 | 2/1989 |
| EP | 0 537 769 A1 | 4/1993 |
| EP | 0 573 273 A2 | 12/1993 |
| EP | 0 592 244 A2 | 4/1994 |
| EP | 0 614 650 A2 | 9/1994 |
| EP | 0 640 329 A1 | 3/1995 |
| EP | 0 677 297 A1 | 10/1995 |
| EP | 0 692 225 A2 | 1/1996 |
| EP | 0 744 162 A2 | 11/1996 |
| EP | 0 797 962 A2 | 10/1997 |
| EP | 0 827 724 A2 | 3/1998 |
| EP | 0 836 838 A1 | 4/1998 |
| EP | 0 927 008 B1 | 7/1999 |
| EP | 0 986 993 A1 | 3/2000 |
| EP | 1 022 031 A1 | 7/2000 |
| EP | 1 060 714 A2 | 12/2000 |
| EP | 1 145 693 A2 | 10/2001 |
| EP | 1 140 244 B1 | 11/2003 |
| FR | 2 682 284 A1 | 4/1993 |
| FR | 2 719 993 A1 | 11/1995 |
| FR | 2 735 015 A1 | 12/1996 |
| GB | 2 226 762 A | 7/1990 |
| JP | H05-329165 A | 12/1993 |
| JP | H07-000430 A | 1/1995 |
| WO | WO 91/07145 A1 | 5/1991 |
| WO | WO 92/13500 A1 | 8/1992 |
| WO | WO 94/01056 A1 | 1/1994 |
| WO | WO 95/07666 A1 | 3/1995 |
| WO | WO 96/03091 A1 | 2/1996 |
| WO | WO 96/39999 A1 | 12/1996 |
| WO | WO 96/41588 A1 | 12/1996 |
| WO | WO 97/02789 A1 | 1/1997 |
| WO | WO 98/37813 A1 | 9/1998 |
| WO | WO 99/03422 A1 | 1/1999 |
| WO | WO 00/15141 A1 | 3/2000 |
| WO | WO 00/15142 A1 | 3/2000 |

(56) References Cited

FOREIGN PATENT DOCUMENTS

| WO | WO 00/42943 A1 | 7/2000 |
|----|----------------|--------|
| WO | WO 01/15625 A1 | 3/2001 |
| WO | WO 01/80773 A1 | 11/2001 |
| WO | WO 02/07648 A1 | 1/2002 |
| WO | WO 02/30482 A1 | 4/2002 |
| WO | WO 02/091950 A1 | 11/2002 |
| WO | WO 03/003947 A1 | 1/2003 |
| WO | WO 03/011183 A2 | 2/2003 |
| WO | WO 03/075799 A1 | 9/2003 |
| WO | WO 03/090643 A1 | 11/2003 |
| WO | WO 2004/006808 A2 | 1/2004 |
| WO | WO 2004/021933 A1 | 3/2004 |
| WO | WO 2004/052421 A1 | 6/2004 |
| WO | WO 2004/060211 A2 | 7/2004 |
| WO | WO 2004/075936 A1 | 9/2004 |

OTHER PUBLICATIONS

International Search Report and Written Opinion mailed Oct. 12, 2021 in connection with International Application No. PCT/US2021/037320.

International Search Report and Written Opinion mailed Sep. 30, 2021, in connection with International Application No. PCT/US2021/037382.

International Search Report and Written Opinion mailed Sep. 30, 2021, in connection with International Application No. PCT/US2021/037338.

* cited by examiner

PROSTHETIC REPAIR FABRIC

FIELD OF DISCLOSURE

The present disclosure relates to a prosthetic repair fabric, and more particularly to a prosthetic repair fabric for use in soft tissue and muscle wall repair.

BACKGROUND

Implantable repair fabrics are employed by surgeons for soft tissue repair and reconstruction, including the repair of anatomical defects such as soft tissue and muscle wall defects. The fabric is typically sutured, stapled, tacked, or otherwise provisionally anchored in place over, under or within the defect. Tissue integration with the fabric, such as tissue ingrowth into and/or along the mesh fabric, eventually completes the repair.

Soft tissue and muscle wall defect repairs may be accomplished using various surgical techniques, including open, plished using various surgical techniques, including open, laparoscopic and hybrid (e.g., Kugel procedure) techniques. During open procedures, a repair fabric is placed through a relatively large incision made in the abdominal wall and layers of tissue and then the defect is filled or covered with the repair fabric. During laparoscopic and hybrid procedures, the fabric may be collapsed, such as by rolling or folding, into a reduced configuration for entry into a subject, either directly through a comparatively smaller incision or through a slender laparoscopic cannula that is placed through the incision.

Various repair fabrics are known and used for repairing soft tissue and muscle wall defects. BARD MESH and VISILEX, available from C.R Bard, are examples of implantable fabrics that have been successfully used in soft tissue and muscle wall repair. Such fabrics are fabricated from polypropylene monofilaments that are knitted into meshes having pores or interstices that promote tissue ingrowth and integration with the fabric.

Scar tissue may form about a repair fabric into a scar plate as tissue ingrowth occurs. The volume and rigidity of the scar plate that forms about the fabric may be affected by various factors, including the amount of foreign material introduced into a patient by the fabric.

It is an object of the disclosure to provide a prosthetic repair fabric for repair of soft tissue and muscle wall defects.

SUMMARY

In one illustrative embodiment, an implantable prosthetic repair fabric comprises a biologically compatible, implantable dual bar warp knit mesh produced according to a first bar pattern chain of 4/2 4/6 4/2 6/8 6/4 6/8 and a second bar pattern chain of 6/8 2/0 6/8 4/2 8/10 4/2. The mesh is knitted of a first monofilament having a first diameter and a second monofilament having a second diameter which is greater than the first diameter. The first monofilament is knitted according to the first bar pattern chain and the second monofilament is knitted according to the second bar pattern chain.

In one illustrative embodiment, an implantable prosthetic repair fabric comprises a knit mesh that includes a plurality of generally polygonal shaped primary pores defined by knitted strands of first filaments. A pair of individual second extend across each primary pore to define a plurality of secondary pores within each primary pore. Each of the pair of second filaments extend substantially parallel to one another. The first filaments having a first diameter and the second filaments having a second diameter which is greater than the first diameter.

In one illustrative embodiment, an implantable prosthetic repair fabric comprises a biologically compatible, implantable dual bar warp knit mesh produced according to a first bar pattern chain of 4/2 4/6 4/2 6/8 6/4 6/8 and a second bar pattern chain of 6/8 2/0 6/8 4/2 8/10 4/2. The mesh has a ball burst strength of 35 lbs to 42.4 lbs, a suture pullout strength of 9 lbs to 11 lbs in the machine direction and 7.5 lbs to 9.5 lbs in the cross direction, and a tensile strength of 11.8 lbs to 16.8 lbs in the machine direction and 34.2 lbs to 47.2 lbs in the cross direction.

DESCRIPTION OF THE DRAWINGS

Various embodiments of the disclosure will now be described, by way of example, with reference to the accompanying drawings, in which.

DETAILED DESCRIPTION

Embodiments of the present disclosure include a prosthetic fabric comprising a mesh fabric that is relatively flexible, thin and light weight and meets the performance and physical characteristics for soft tissue repair and reconstruction procedures. The surgical repair fabric may be used for reinforcing and closing soft tissue defects, and is particularly indicated for chest wall reconstruction and/or the repair of hernias, such as inguinal hernias. The mesh fabric is formed of a biologically compatible, flexible and strong implantable material.

The mesh fabric may employ a knit construction that provides relatively large openings or pores to ensure good visibility of the underlying anatomy without sacrificing mechanical properties of the mesh. The porous character of the fabric allows tissue infiltration to incorporate the prosthetic. The knitted fabric is sufficiently strong and structured to prevent or minimize potential pullout of anchoring fasteners, such as sutures, staples, tacks, and the like. The flexible repair fabric may promote an easy reduction in size for entry into the subject. In this manner, the flexible fabric may be collapsed into a slender configuration, such as a roll, which can be supported in, and advanced through, a narrow laparoscopic cannula for use in laparoscopic procedures.

The mesh fabric employs a relatively lighter weight, thinner, and/or more flexible fabric construction that may introduce less foreign body material into a patient as compared to other repair fabrics. The porous prosthetic repair fabric allows a prompt fibroblastic response through the interstices of the mesh, forming a secure fibrous/prosthetic layer. The fabric may promote a thinner and more compliant scar plate that may result in a relatively more comfortable soft tissue or muscle wall repair for a patient.

Figure 1:
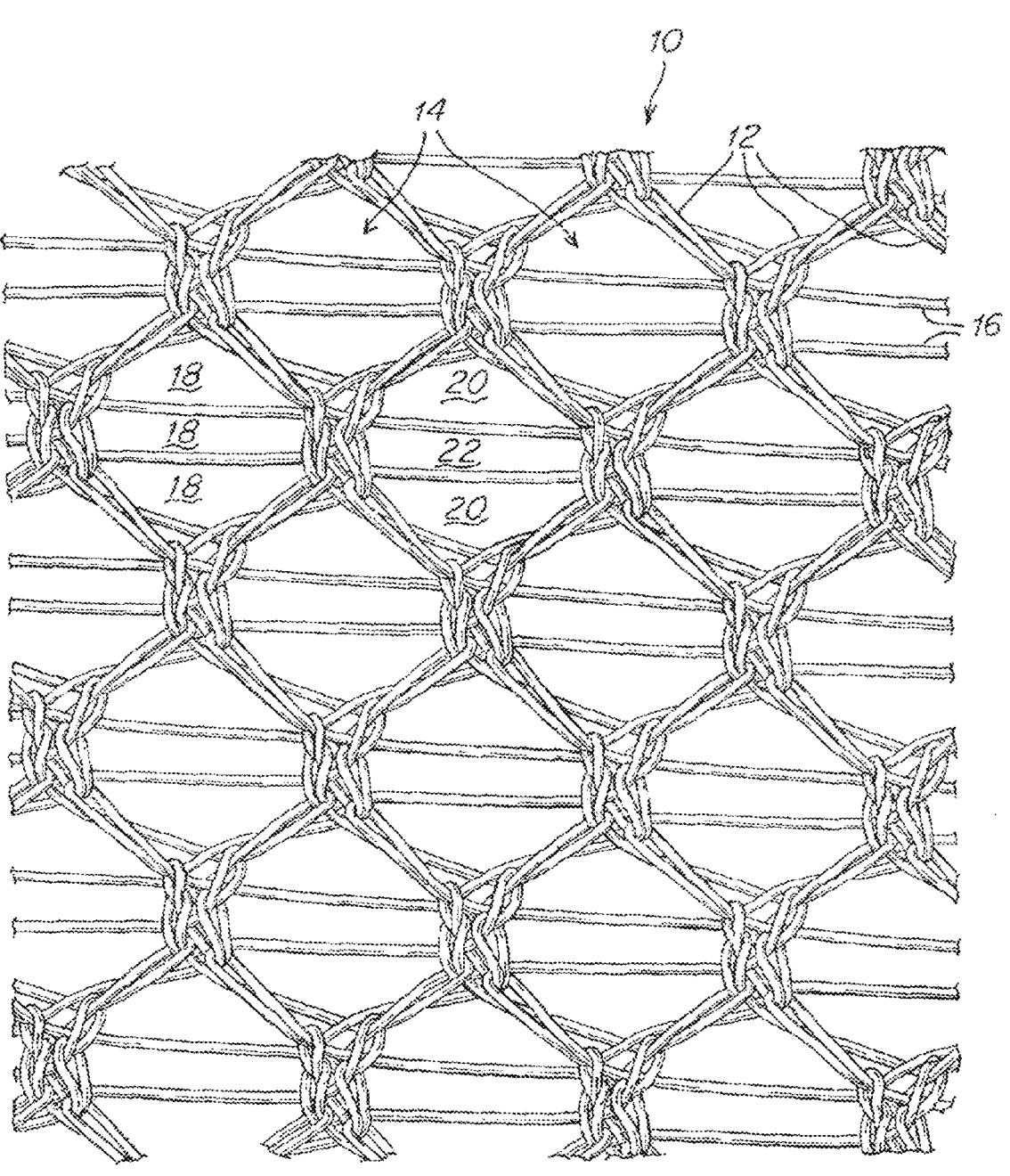
FIG. 1 is an enlarged plan view of a dual bar warp knit, mesh fabric according to an illustrative embodiment of the present disclosure.

In one illustrative embodiment shown in FIG. 1, the repair fabric comprises a knit mesh 10 including knitted strands of filaments 12 that define larger, primary pores 14 arranged in a uniform pattern. A pair of individual filaments 16 extend across the primary pores to define a plurality of smaller, secondary pores 18 therein.

In the illustrated embodiment, the primary pores 14 are bounded by knitted strands of filaments 12. However, it is to be appreciated that one of more boundaries of the primary pores 14 may be defined by individual filaments as would be apparent to one of skill in the art. As shown, the primary pores 14 may have a generally polygon shape, such as hexagon, diamond or square shaped, although aspects of the disclosure are not limited. In this regard, it is to be understood that other pore shapes are also contemplated, including, but not limited to, circular, non-circular, round, oval and the like, as would be apparent to one of skill in the art.

The prosthetic repair fabric may be constructed to increase flexibility and/or reduce the overall weight per unit area of the fabric. Such properties may facilitate an easier collapse of the repair fabric for introduction into a patient. These properties may also provide for easier manipulation of the repair fabric about the surgical site within the patient. In one illustrative embodiment, the primary pores 14 have an area of approximately 0.01032 to 0.01233 square inches. In this regard, less material may be used to produce a given area of mesh, which may result in a reduced weight mesh. Additionally, the generally greater spacing between the strands of filaments 12 that are associated with the larger primary pores 14 may also contribute to a more flexible mesh. It is to be appreciated, however, that the size of the primary pores may vary as would be apparent to one of skill in the art, as aspects of the disclosure are not limited in this respect.

For some applications, it may be desirable to provide secondary pores 18 within the primary pores 14. In one illustrative embodiment shown in FIG. 1, each primary pore 14 is subdivided into a plurality of secondary pores 18 by a pair of individual or single filaments 16. In the illustrative embodiment, the pair of filaments 16 divides the primary pore 14 into a pair of generally triangular secondary 20 pores and a generally rectangular secondary pore 22 that is positioned between the two generally triangular secondary pores 20. It is to be appreciated, however, that the shapes of secondary pores and/or numbers of secondary pores within each primary pore, if desired, may vary as would be apparent to one of skill in the art, as aspects of the disclosure are not limited in this respect.

In one illustrative embodiment as shown in FIG. 1, the pair of individual filaments 16 extend substantially parallel to one another across the primary pores 14. As illustrated, the pair of parallel filaments 16 may be generally in linear alignment with corresponding pairs of filaments in adjacent primary pores. However, it is to be understood that the individual filaments may be positioned and oriented in other suitable arrangements, as aspects of the present disclosure are not limited in this respect.

The prosthetic repair fabric may be constructed so as to be provisionally anchored to tissue or muscle using a wide variety of fasteners, such as sutures, staples, spiral tacks, Q-rings and the like. The individual filaments 16 that extend across the primary pores may provide additional features for engaging the fasteners used to anchor the fabric. It is to be appreciated that repair fabrics may be anchored to tissue and/or mesh with fasteners, such as spiral tacks and Q-ring constructs, that have relatively small features for engaging and holding the repair fabric in place. The smaller, secondary pores 18 associated with the individual filaments may provide for improved engagement with the fasteners in a manner that is sufficiently strong and structured to prevent or minimize pullout. It is to be appreciated that the size of the secondary pores may vary as would be apparent to one of skill in the art, as aspects of the disclosure are not limited in this respect.

The knit mesh may employ filaments having the same size or different relative sizes to adjust mechanical properties of the fabric. In one illustrative embodiment, the mesh fabric may include first filaments 12 having a first diameter to form the primary pores and second filaments 16 having a second diameter that is different from the first diameter extending across the primary pores. In one embodiment, the second filaments 16 have a second diameter that is greater than the first diameter of the first filaments. Such an arrangement may enhance the handling of the mesh fabric by increasing its stiffness. It is to be appreciated, however, that other arrangement are contemplated. For example, and without limitation, the diameter of the first filaments 12 may be greater than the diameter of the second filaments 16.

In one illustrative embodiment, the knit mesh 10 may be produced in a lapping pattern by using two partially threaded guide bars to knit the pattern over three needles in a six course repeat. The fabric structure may be of an atlas type where each knitted end travels more than two needles, which may prevent unraveling of the mesh.

Figures 2A, 2B:
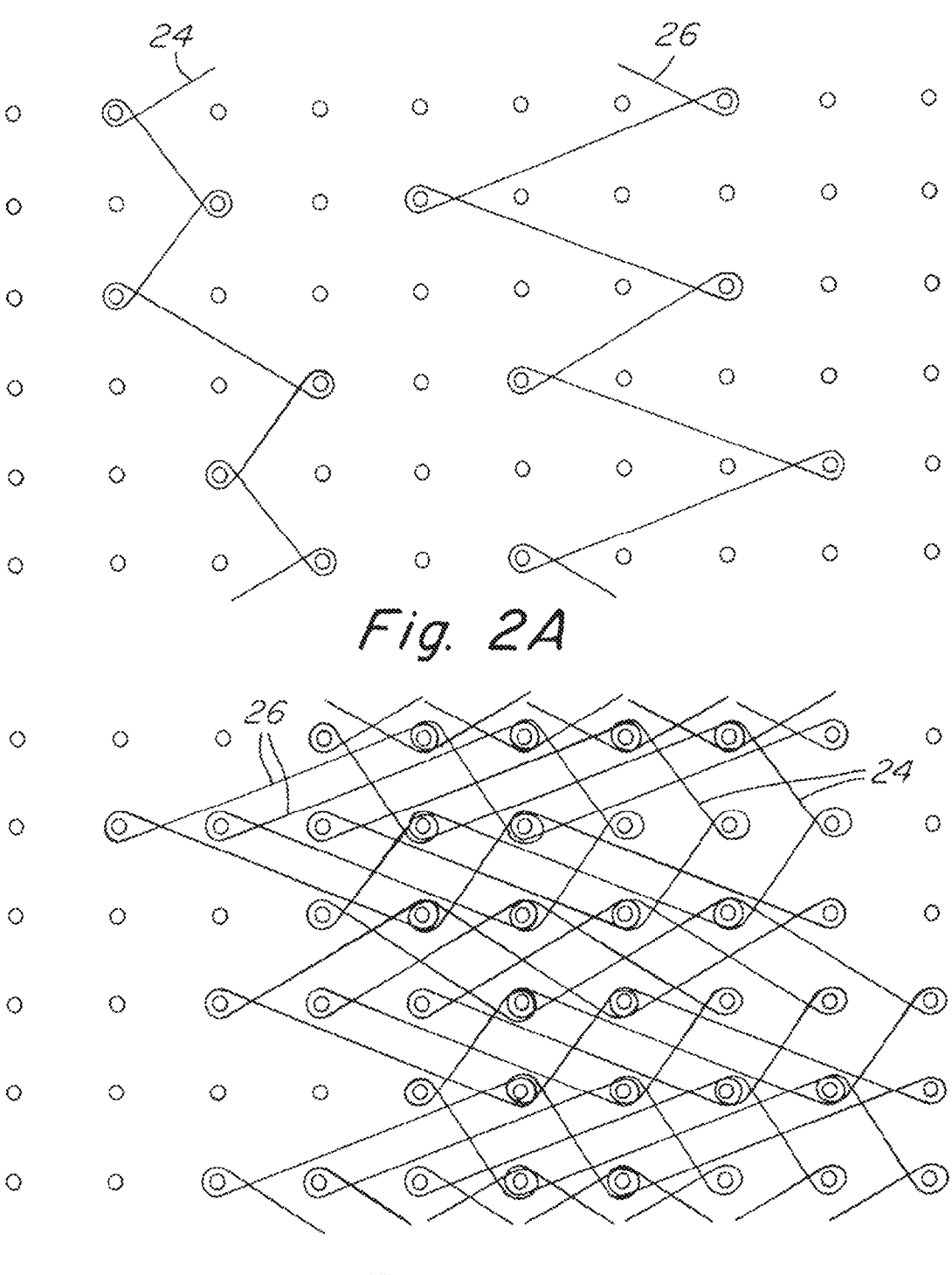
FIGS. 2A-2B illustrate the chain lapping pattern for the mesh fabric of FIG. 1.

In one illustrative embodiment shown in FIG. 2, the repair fabric may employ a dual bar warp knit mesh structure produced using two guide bars moving according to a first bar pattern chain of 4/2 4/6 4/2 6/8 6/4 6/8 (identified as reference 24) and a second bar pattern chain of 6/8 2/0 6/8 4/2 8/10 4/2 (identified as reference 26). The mesh may be knitted on a single needle bar, 24 gauge Rachelle knitting machine. The mesh may be fabricated with approximately 34 to 36 courses per inch and approximately 12 to 17 wales per inch. It is to be appreciated, however, that the mesh fabric may be knitted using any suitable knit pattern as would be apparent to one of skill in the art, as aspects of the disclosure are not limited in this respect.

The knit mesh may be produced at various widths apparent to one of skill in the art, such as from 1 inch to 80 inches, depending on the intended application for which the repair fabric is being produced.

Following knitting, the fabric may be washed to remove foreign matter, such as residual processing lubricant. A cleaning agent, such as Triton X-100, may be used to aid in the removal of such foreign matter. Following washing, the mesh may be dried at a temperature lower than the heat set and melt temperatures of the material, as would be apparent to one of skill in the art.

Embodiments of the knit mesh may be heat set to impart a shape memory to the mesh and the prosthetic fabric formed of the mesh. In one illustrative embodiment, the fabric is heat set to have a generally planar shape memory. In this manner, after the fabric is collapsed and inserted into a patient, the fabric may revert back to the planar configuration for appropriate placement against tissue of the patient. It is to be appreciated that other embodiments of the fabric may be provided with a shape memory that corresponds to configurations different than planar, or to have no shape memory at all, as aspects of the disclosure are not limited in this regard.

If desired, the knit mesh may be heat set under tension, in a crochet hoop or tentering frame. The heat set may be applied while the mesh knit is being stretched in a particular direction to help set the mesh into a particular configuration. In one illustrative embodiment, the knit mesh is stretched in the cross machine knit direction and simultaneously allowed to partially relax or contract in the machine direction to a fixed point while heat is applied to set the mesh. It is to be understood, however, that other techniques apparent to one of skill in the art may be used to heat set the knit mesh, as aspects of the disclosure are not limited in this respect.

For some applications, it may be desirable to smooth the knitted mesh to reduce the texture or surface roughness of the mesh. In one illustrative embodiment, the knitted mesh is lightly pressed between a pair of plates which includes a heated plate that is pressed against the rough surface of the mesh to reduce high spots of the mesh and to heat set it to smooth its surface. It is to be appreciated, however, that the fabric may be smoothed using any suitable process apparent to one of skill in the art. For example, the fabric may be smoothed by passing the knitted mesh between a pair of heated rollers during the washing and drying process.

The filaments that are used to fabricate the repair fabric may contribute to the resulting mechanical properties of the fabric. In one illustrative embodiment, the repair fabric is knitted with first filaments 12 having a diameter of approximately 0.0045 to 0.0051 inches (first bar pattern chain), and preferably a diameter of approximately 0.0048 inches, and second filaments 16 having a diameter of approximately 0.0063 to 0.0075 inches (second bar pattern chain), and preferably a diameter of approximately 0.0075 inches. Filaments of these diameters may contribute to an enhanced handling and increased strength properties of the overall repair fabric. It is to be understood, however, that the fabric may be fabricated with filaments having any suitable diameter apparent to one of skill in the art that is suitable for a desired application, as aspects of the disclosure are not limited in this respect.

In one illustrative embodiment, the fabric has a thickness of approximately 0.022 to 0.024 inches, and preferably a thickness of approximately 0.0225 to 0.0235 inches. In one illustrative embodiment, the fabric has a weight per unit area of approximately 0.066 to 0.069 grams per square inch. It is to be appreciated, however, that the fabric may be fabricated to have any thickness and/or weight per unit area apparent to one of skill in the art that is suitable for a desired application, as aspects of the disclosure are not limited in this respect.

In one illustrative embodiment, the filaments used to fabricate the mesh fabric comprise a polypropylene monofilament, which is inert in the presence of infection, is non-wettable and has a low foreign body reaction. In one illustrative embodiment, the monofilaments are formed of Aran Biomedical ProTex Med Polypropylene resin PPS50156 and PPS50157. In one embodiment, the first monofilament has a denier of approximately 98±11 and the second monofilament has a denier of approximately 240±20. In one embodiment, the first and second monofilaments have a tenacity of approximately 6.0 to 8.5 grams/denier, with a nominal tenacity of approximately 6.2 grams/denier. It is to be appreciated, however, that filaments of different configurations, properties and/or materials may be employed to fabricate the fabric. For example, the filaments may comprise multifilaments or monofilaments having different mechanical characteristics as would be apparent to one of skill in the art, as aspects of the present disclosure are not limited in this respect.

EXAMPLES

The following examples are illustrative only and are not intended to limit the scope of the present disclosure.

Physical properties of a representative two bar warp knit mesh fabric produced from 0.0048 inch (first bar) and 0.0075 inch (second bar) polypropylene monofilament according to the illustrative embodiment shown in FIGS. 1 and 2 (labeled Embodiment #1 in Table 1) were evaluated and compared to several known mesh fabrics (comparative mesh fabrics). Physical and performance characteristics were tested including mesh thickness, pore size, mesh weight per unit area, suture pull out strength, burst strength, tear resistance, tensile (break) strength and elongation at break, and stiffness. Testing methodology and results appear below in Table 1, where mean results and ranges are reported from several test samples (ranges appear in parentheses).

Suture Pullout Strength: A sample of mesh measuring at least 1 inch×1 inch (Embodiment #1) or at least 0.5 inch×3 inches (comparative mesh fabrics) was prepared and clamped in the lower jaw of an MTS™ or equivalent tensile test machine. The long dimension of the sample should be parallel with its orientation designation (machine or cross-machine). At least 0.5 inch (Embodiment #1) or at least 1 inch (comparative mesh fabrics) of the mesh was exposed above the jaw. A spring steel wire with a diameter of approximately 0.019 inches was placed through the mesh to simulate a suture. The wire was placed 5±1 mm from the edge of the mesh. The wire suture was looped back and both ends were attached to the upper jaw of the tensile machine. The suture was then pulled at a rate of 5 inches per minute through the mesh. The peak force was recorded for 4 to 10 samples tested in both the machine and cross directions of the mesh and the average force was calculated for at least 10 total measurements in each direction.

Pore Size: A sample of mesh was placed on an optical coordinate measurement device such as a Tesa Vision (35×) or equivalent.

Figure 3:
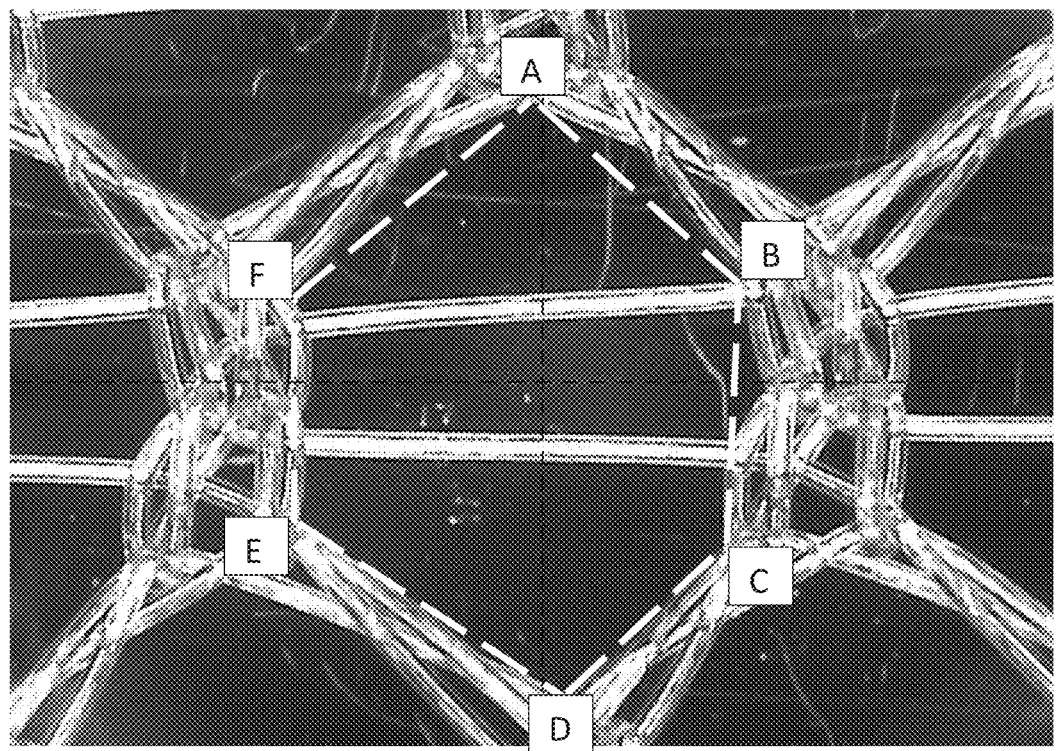
FIG. 3 is a schematic illustration for determining the area of a primary cell.

For embodiment #1, each primary pore has a generally hexagon shape which contains two generally triangular pores and a generally rectangular pore in the middle section. The length L of each leg of the primary pore was measured dimensionally between each pair of end points A-B, B-C, C-D, D-E, E-F and F-A, as illustrated by dashed lines in FIG. 3. The pore area of the primary pore was calculated based on the area of a hexagon as follows, where $L_{average}$ is the average length of each leg:

$$Area = (L_{average})^2 \times (3\sqrt{3})/2$$

Three randomly selected primary cells (not counting the pores formed by the loops or knots) of each of four mesh samples were measured and a combined average was calculated.

Tensile (Break) Strength and Elongation at Break: A mesh sample measuring approximately 1 inch×6 inches was placed into the pneumatic jaws of an MTS™ tensile tester or equivalent device. The sample was oriented so that the knit direction being tested was parallel to the 6 inch length. The ends of the 6 inch sample were gripped in the lower and upper jaws of the tester. Starting with a minimum separation of 2 inches, the sample was pulled at a constant rate of 12 inches per minute until the sample broke. The peak load and elongation at break were recorded. The samples were tested in both the cross direction and the machine direction. The averages of at least 10 total measurements taken from 4 to 10 samples were then calculated for each direction.

Mesh Thickness: A sample of mesh was measured using a standard thickness snap gage with an approximate 0.38 inch diameter pressure foot that is lightly spring loaded. The thickness was measured by lowering the foot onto the mesh. Measurements were taken to the nearest 0.0001 inch. At least five sheets of mesh were measured in total and a combined average was calculated.

Mesh Weight/Unit Area: Using a sample size of at least four pieces of mesh that measured at least approximately 2 inches×2 inches, the weight of each sample was measured in grams to the nearest 0.0001 gram. The area was calculated by measuring the length and width dimensions taken to the nearest 0.001 inch, minus the area of any radiused corner. The weight per unit area was calculated for each sample using the weight and unit area. The average weight per unit area was calculated by combining and averaging the weight per unit area for each sample.

Burst Strength: This test method was derived from the ANSI/AAMI VP20-1994 Section 8.3.3.2 and ASTM Ball Burst method D3787-01. A mesh sample was placed on top of a circular O-ring measuring approximately 1 inch in diameter. The O-ring was seated in a grooved plate in a fixture with a hole in the middle of plate containing the O-ring. The fixture was attached to the lower jaw in an MTS™ or equivalent test machine. The plate with the mesh was raised and clamped against an upper plate in the fixture, compressing the mesh sample. The upper plate also contained a hole with the same diameter as the lower plate. The holes in the fixture plates are dimensioned to be just slightly larger than and to accept a rounded ball tipped rod that has a 0.38 inch diameter tip. The rod was connected to an upper jaw of the test machine that was moved down through the sample at a constant rate of 12 inches per minute. The peak load was recorded for at least 10 samples. The average burst strength was then calculated based on the peak loads for the samples.

Tear Resistance: A mesh sample measuring approximately 2 inches×2 inches was prepared. A 1 inch slit was cut in one side (the direction to be tested) at the midpoint to form two mesh sections. One section of mesh was clamped in the lower jaw of a pneumatic fixture and the other was clamped in the top jaw of the fixture. Starting with the jaws at a minimum spacing of 1 inch, the mesh was pulled at a rate of 12 inches per minute until the tear was completed. The peak force was recorded. Samples were tested in the cross direction and the machine direction (Embodiment #1), and the cross direction, the machine direction, and the diagonal direction (comparative mesh fabrics). The averages of at least 10 total measurements taken from 4 to 10 samples were then calculated for each group direction.

TABLE I

| | Embodiment #1 | BARD Soft Mesh | BARD MESH | Ethicon PROLENE Soft Mesh | Ethicon MERSILENE Mesh |
|---|---|---|---|---|---|
| Suture Pullout (lbs) | | | | | |
| Machine Direction | 10.2 (6.1 to 12.9) | 8.2 (7.1-9.6) | 12.16 (9.14-14.29) | 5.4 (3.9-6.6) | 1.75 (1.33-2.33) |
| Cross Direction | 8.5 (3.2-15.0) | 6.7 (4.8-8.0) | 7.97 (6.87-9.73) | 6.3 (5.2-8.0) | 2.17 (1.53-2.47) |
| Pore Size (inches$^2$) | | | | | |
| Large Cell | 0.01093 (0.01032-0.01233) | 0.00975 (0.00891-0.01033) | n/a | 0.00941 (0.00803-0.0104) | n/a |
| Small Pore | n/a | 0.00246 (0.00220-0.00320) | 0.00085 (0.00062-0.00100) | 0.00386 (0.00357-0.00432) | 0.00123 (0.00104-0.00139) |
| Tensile (Break) Strength (lbs) | | | | | |
| Machine Direction | 14.3 (9.5 to 16.2) | 11.93 (10.07-15.20) | 21.7 (13.9-26.8) | 22.11 (18.01-26.8) | 22.7 (20.3-26) |
| Cross Direction | 40.7 (28.3 to 52.2) | 43.84 (35.26-48.38) | 49.9 (42.7-58.0) | 21.97 (19.00-26.01) | 10.5 (8.9-12) |
| Elongation at Break (%) | | | | | |
| Machine Direction | 77.4 (68-86.5) | 61.8 (26.0-94.5) | 43 (30-50) | 69.25 (59-79.5) | 24 (22-26) |
| Cross Direction | 34.7 (20-40) | 49 (40.5-54) | 30 (25-35) | 54.5 (49.5-63.5) | 25 (21-29) |
| Mesh Thickness (Inches) | | | | | |
| | 0.0229 (0.0225-0.0235) | 0.0174 (0.0168-0.0172) | 0.0278 (.0273-0.0296) | 0.0168 (0.0163-0.0172) | 0.0203 (0.0200-0.0204) |
| Weight/Unit Area (gms/inches$^2$) | | | | | |
| | 0.0671 (0.0661-0.0690) | 0.0282 (0.0274-0.0293) | 0.0680 (0.065-0.071) | 0.0287 (0.0273-0.0296) | 0.0274 (0.026-0.030) |
| Tear Resistance (lbs) | | | | | |
| Machine Direction | 8.69 (7.37-10.33) | 6.36 (5.35-6.96) | 10.31 (7.27-14.68) | 6.05 (4.70-7.15) | 1.53 (1.33-1.87) |
| Cross Direction | 9.60 (7.38-10.93) | 5.46 (4.84-6.30) | 11.01 (9.41-13.68) | 5.72 (4.78-6.43) | 1.50 (1.33-1.74) |
| Diagonal Direction | n/a | 5.94 (5.18-6.82) | 10.83 (7.20-14.26) | 5.97 (5.27-6.65) | 1.44 (1.27-1.60) |
| Ball Burst (⅜" ball, lbs) | | | | | |
| | 36.82 (27.24-42.38) | 29.17 (25.02-34.94) | 67.98 (63.64-74.21) | 31.01 (26.58-35.13) | 18.1 (16.0-19.4) |
| Mesh Construction | | | | | |
| Courses (per inch) | 36 | 34.6 | 54.5 | 45.6 | 72 |

TABLE I-continued

| | Embodiment #1 | BARD Soft Mesh | BARD MESH | Ethicon PROLENE Soft Mesh | Ethicon MERSILENE Mesh |
|---|---|---|---|---|---|
| Wales (per inch) | 14 (13.5-14.5) | (34-36) 14.1 (12-17) | 15.5 | (44-48) 16.2 (16-18) | 47 |

It should be understood that the foregoing description of the disclosure is intended merely to be illustrative thereof and that other equivalents, embodiments and modifications of the disclosure are within the scope of the disclosure recited in the claims appended hereto.

What is claimed is:

1. An implantable prosthetic repair fabric, comprising:
a biologically compatible, implantable dual bar warp knit mesh produced according to a first bar pattern chain of 4/2 4/6 4/2 6/8 6/4 6/8 and a second bar pattern chain of 6/8 2/0 6/8 4/2 8/10 4/2, the mesh is knitted of a first monofilament having a first diameter and a second monofilament having a second diameter which is greater than the first diameter, the first monofilament being knitted according to the first bar pattern chain and the second monofilament being knitted according to the second bar pattern chain.

2. The implantable prosthetic repair fabric according to claim 1, wherein the first and second monofilaments include polypropylene monofilament.

3. The implantable prosthetic repair fabric according to claim 1, wherein the first monofilament has a diameter of approximately 0.0045 to 0.0051 inches and the second monofilament has a diameter of approximately 0.0063 to 0.0075 inches.

4. The implantable prosthetic repair fabric according to claim 3, wherein the first monofilament has a diameter of approximately 0.0048 inches and the second monofilament has a diameter of approximately 0.0075 inches.

5. The implantable prosthetic repair fabric according to claim 1, wherein the first monofilament has a denier of approximately 98±11 and the second monofilament has a denier of approximately 240±20.

6. The implantable prosthetic repair fabric according to claim 1, wherein the first and second monofilaments have a tenacity of approximately 6.00 to 8.50 grams per denier.

7. The implantable prosthetic repair fabric according to claim 6, wherein the first and second monofilaments have a tenacity of approximately 6.2 grams per denier.

8. The implantable prosthetic repair fabric according to claim 1, wherein the mesh has a knit construction that includes approximately 34 to 36 courses per inch and approximately 12 to 17 wales per inch.

9. The implantable prosthetic repair fabric according to claim 1, wherein the mesh has a weight per unit area of approximately 0.0661 to 0.0690 grams per square inch.

10. The implantable prosthetic repair fabric according to claim 1, wherein the mesh has a thickness of approximately 0.022 to 0.024 inches.

11. The implantable prosthetic repair fabric according to claim 1, wherein the mesh has a ball burst strength of 35 lbs to 42.4 lbs.

12. The implantable prosthetic repair fabric according to claim 11, wherein the mesh has a ball burst strength of 36 lbs to 40 lbs.

13. The implantable prosthetic repair fabric according to claim 12, wherein the mesh has a ball burst strength of 36 lbs to 39 lbs.

14. The implantable prosthetic repair fabric according to claim 1, wherein the mesh has a suture pullout strength of 9 lbs to 11 lbs in the machine direction and 7.5 lbs to 9.5 lbs in the cross direction.

15. The implantable prosthetic repair fabric according to claim 14, wherein the mesh has a suture pullout strength of approximately 10.2 lbs in the machine direction and approximately 8.5 lbs in the cross direction.

16. The implantable prosthetic repair fabric according to claim 1, wherein the mesh has a tensile strength of 11.8 lbs to 16.8 lbs in the machine direction and 34.2 lbs to 47.2 lbs in the cross direction.

17. The implantable prosthetic repair fabric according to claim 16, wherein the mesh has a tensile strength of approximately 14.3 lbs in the machine direction and approximately 40.7 lbs in the cross direction.

18. An implantable prosthetic repair fabric, comprising:
a knit mesh that includes a plurality of generally polygonal shaped primary pores defined by knitted strands of first filaments having a first diameter; and
a pair of individual second filaments that extend across each primary pore to define a plurality of secondary pores within each primary pore, each of the pair of individual second filaments extending substantially parallel to one another, each of the second filaments having a second diameter which is greater than the first diameter.

19. The implantable prosthetic fabric according to claim 18, wherein each primary pore has an area of approximately 0.0103 to 0.0123 square inches.

20. The implantable prosthetic fabric according to claim 18, wherein the primary pores are generally hexagonal shaped.

21. The implantable prosthetic repair fabric according to claim 18, wherein the mesh is formed of knitted first and second monofilaments.

22. The implantable prosthetic repair fabric according to claim 21, wherein the first and second monofilaments include polypropylene monofilament.

23. The implantable prosthetic repair fabric according to claim 22, wherein the first monofilament has a diameter of approximately 0.0045 to 0.0051 inches and the second monofilament has a diameter of approximately 0.0063 to 0.0075 inches.

24. The implantable prosthetic repair fabric according to claim 22, wherein the first monofilament has a diameter of approximately 0.0048 inches and the second monofilament has a diameter of approximately 0.0075 inches.

25. The implantable prosthetic repair fabric according to claim 22, wherein the first monofilament has a denier of approximately 98±11 and the second monofilament has a denier of approximately 240±20.

26. The implantable prosthetic repair fabric according to claim 22, wherein the first and second monofilaments have a tenacity of approximately 6.00 to 8.50 grams per denier.

27. The implantable prosthetic repair fabric according to claim 22, wherein the first and second monofilaments have a tenacity of approximately 6.2 grams per denier.

28. The implantable prosthetic repair fabric according to claim 18, wherein the mesh has a knit construction that includes approximately 34 to 36 courses per inch and approximately 12 to 17 wales per inch.

29. The implantable prosthetic repair fabric according to claim 18, wherein the mesh has a weight per unit area of approximately 0.0661 to 0.0690 grams per square inch.

30. The implantable prosthetic repair fabric according to claim 18, wherein the mesh has a thickness of approximately 0.022 to 0.024 inches.

31. An implantable prosthetic repair fabric, comprising:
a biologically compatible, implantable dual bar warp knit mesh produced according to a first bar pattern chain of 4/2 4/6 4/2 6/8 6/4 6/8 and a second bar pattern chain of 6/8 2/0 6/8 4/2 8/10 4/2, the mesh having a ball burst strength of 35 lbs to 42.4 lbs, a suture pullout strength of 9 lbs to 11 lbs in the machine direction and 7.5 lbs to 9.5 lbs in the cross direction, and a tensile strength of 11.8 lbs to 16.8 lbs in the machine direction and 34.2 lbs to 47.2 lbs in the cross direction.

32. The implantable prosthetic repair fabric according to claim 31, wherein the mesh has a ball burst strength of 36 lbs to 39 lbs.

33. The implantable prosthetic repair fabric according to claim 31, wherein the mesh has a suture pullout strength of approximately 10.2 lbs in the machine direction and approximately 8.5 lbs in the cross direction.

34. The implantable prosthetic repair fabric according to claim 31, wherein the mesh has a tensile strength of approximately 14.3 lbs in the machine direction and approximately 40.7 lbs in the cross direction.

35. The implantable prosthetic repair fabric according to claim 31, wherein the mesh is knitted of a first monofilament having a first diameter and a second monofilament having a second diameter which is greater than the first diameter, the first monofilament being knitted according to the first bar pattern chain and the second monofilament being knitted according to the second bar pattern chain.

36. The implantable prosthetic repair fabric according to claim 31, wherein the mesh has a knit construction that includes approximately 34 to 36 courses per inch and approximately 12 to 17 wales per inch.

37. The implantable prosthetic repair fabric according to claim 31, wherein the mesh has a weight per unit area of approximately 0.0661 to 0.0690 grams per square inch.

38. The implantable prosthetic repair fabric according to claim 31, wherein the mesh has a thickness of approximately 0.022 to 0.024 inches.

\* \* \* \* \*